United States Patent [19]

Vaughan

[11] 4,303,551
[45] Dec. 1, 1981

[54] SUPPORTED CATALYST
[75] Inventor: Ronald J. Vaughan, Orinda, Calif.
[73] Assignee: Varen Technology, Marshallton, Del.
[21] Appl. No.: 155,797
[22] Filed: May 30, 1980

Related U.S. Application Data

[63] Continuation-in-part of Ser. No. 970,475, Dec. 18, 1978, abandoned, Ser. No. 660,634, Feb. 23, 1976, and Ser. No. 132,149, Mar. 20, 1980, which is a continuation-in-part of Ser. No. 970,474, Dec. 18, 1978, abandoned.

[51] Int. Cl.$^3$ ............................................. B01J 31/06
[52] U.S. Cl. .................................. 252/430; 252/426; 252/477 R
[58] Field of Search ..................... 252/426, 430, 477 R

[56] References Cited

U.S. PATENT DOCUMENTS

| | | | |
|---|---|---|---|
| 3,041,317 | 6/1962 | Gibbs et al. | 526/243 |
| 3,169,142 | 2/1965 | Knagos et al. | 260/457 |
| 3,177,229 | 4/1965 | Leak et al. | 252/477 R X |
| 3,282,875 | 11/1966 | Connolly et al. | 260/29.6 |
| 3,499,797 | 3/1970 | Hooper | 252/477 R X |
| 3,624,053 | 11/1971 | Gibbs et al. | 260/543 F X |
| 3,882,093 | 5/1975 | Cavanaugh | 260/614 F X |
| 4,022,847 | 5/1977 | McClure | 585/747 |
| 4,038,213 | 7/1977 | McClure et al. | 252/430 |
| 4,052,475 | 10/1977 | McClure et al. | 585/470 |

OTHER PUBLICATIONS

"Innovation", vol. 4, No. 3 (Spring 1973) pp. 10–13, Pub. by DuPont.
Grot et al. "Perfluorinated Ion Exchange Members", paper presented to 141st National Meeting, The Electrochemical Soc., May, 1972.
"Nafion Perfluorosulfonic Acid Products", a Du Pont brochure, Feb. 1976.
"Nafion Perfluorosulfonic Acid Membranes for Use in Chlorine and Caustic Soda Production Systems", a Du Pont brochue, Aug. 1977.
"The Commercialization of Ion Exchange Membranes to Produce Chlorine and Caustic Soda", paper presented at the Electrochemical Soc. Fall Meeting, Oct. 1977.
"Prediction of the Molecular Structure of Nafion under Different Physicochemical Conditions", paper presented at Electrochemical Soc. Fall Meeting, Oct. 1977.
Ukihashi, "A Membrane for Electrolysis", Chemtech, Feb. 1980, pp. 118–120.

*Primary Examiner*—Patrick Garvin
*Attorney, Agent, or Firm*—Charles J. Tonkin

[57] ABSTRACT

A solid fluorocarbon polymer containing pendant sulfonic acid groups and supported on a solid substrate is prepared using an intermediate which is either thermoplastic or soluble to a measurable extent in a solvent. The intermediate is formed into the desired shape and then the intermediate is converted as desired to the sulfonic acid form for use as a catalyst. A preferred embodiment is a solid polymeric acid catalyst consisting essentially of a thin film, less than 2 mils thick, of a solid perfluorocarbon polymer containing pendant acid groups and supported on the surface of a solid impermeable substrate such as a heat conductive metallic composition.

15 Claims, No Drawings

SUPPORTED CATALYST

This patent application is a continuation-in-part of U.S. Ser. No. 970,475, filed Dec. 18, 1978 and now abandoned, of U.S. Ser. No. 660,634, filed Feb. 23, 1976, and of U.S. Ser. No. 132,149, filed Mar. 20, 1980 (which is a continuation-in-part of U.S. Ser. No. 970,474, filed Dec. 18, 1978 and now abandoned), all in the name of Ronald J. Vaughan.

FIELD OF THE INVENTION

This invention relates to a method for preparing a solid, supported catalyst comprising a perfluorocarbon polymer containing pendant sulfonic acid groups.

BACKGROUND OF THE INVENTION

Solid perfluorocarbon polymers containing pendant sulfonic acid groups are useful catalysts for alkylating aliphatic or aromatic hydrocarbons, for decomposing organic hydroperoxides, such as cumene hydroperoxide, for sulfonating or nitrating organic compounds, and for oxyalkylating hydroxylic compounds.

A serious drawback to the commercial use of the perfluorocarbon sulfonic acid catalysts has been their high cost. As a means of reducing costs and improving effectiveness, films of the catalyst are desirable because they permit better control of catalytic activity and easier management of heats-of-reaction and in some instances, better selectivity. However, the solid perfluorocarbon sulfonic acids catalysts at the desired molecular and equivalent weights are difficult to work with because they are not thermoplastic, that is, they do not melt or soften on heating. In addition, such perfluorocarbon sulfonic acids having equivalent weights higher than about 900 and molecular weights in the range of about 50,000 to 100,000 daltons are substantially insoluble in all solvents. Polymers having equivalent weights below about 900 and in the lower range of molecular weights of about 50,000 daltons or lower are soluble in organic solvents i.e., ethanol, isopropanol, cyclohexanol and mixtures of organic solvents and water. It is known in polymer art that crosslinking polymer structures with free radicals and bifunctional compounds can substantially insolubilize low molecular weight polymers. It is also known that perfluorocarbon polymers tend to degrade in molecular weight and not crosslink with free radicals. The perfluorocarbon polymers containing pendant sulfonic acid groups form salts with metal ions which are less soluble in most solvents than the sulfonic acid polymer but the sulfonate salts of the perfluorocarbon polymer are not effective strong acid catalyst. There is no known way to deposit a soluble perfluorosulfonic acid polymer from a solution onto a support and then insolubilize the perfluorosulfonic acid polymer with retention of catalytic activity. The supported perfluorosulfonic acid catalyst of McClure et al. U.S. Pat. No. 4,038,213 made by depositing from a solution the soluble low equivalent weight, low molecular weight perfluorosulfonic acid resins are substantially limited in use to anhydrous systems i.e., hydrocarbons without organic solvents. An embodiment of the instant invention is an improved process for making supported perfluorosulfonic acid catalyst. This embodiment comprises conversion of the sulfonic acid groups to the quaternary ammonium or phosphonium salts to effect solubility of polymers having equivalent weights above 1,000 and molecular weights about about 50,000 daltons, deposition of the polymer containing the quaternary ammonium and phosphonium salts on a support, then, conversion of the ammonium and phosphonium salts to the sulfonic acid.

Another embodiment of the instant invention is a process for making new and improved supported perfluorosulfonic acid catalyst wherein the desired catalyst is obtained by first forming into the desired catalyst shape or coating on a substrate, as an intermediate or precursor material, a polymer of perfluorocarbon containing a sulfonyl fluoride group. Then the shaped polymer or coating is converted, to the degree desired, into the perfluorocarbon sulfonic acid catalyst to obtain a composite structure comprising a thin film of the perfluorosulfonic acid resin, a thin film of the intermediate or precursor material and a support. The forming is by heating if the intermediate polymer or precursor material is shaped as a thermoplastic, or by dissolving the intermediate polymer or precursor material in a solvent and then forming a coating on a substrate by evaporative deposition. The intermediate or precursor sulfonyl fluoride film serves to firmly bond the perfluorosulfonic acid catalyst to the support and to substantially insolubilize normally soluble low equivalent weight, low molecular weight perfluorosulfonic acid molecules on the surface of the perfluorosulfonyl fluoride or intermediate material, presumably by molecular entanglement of the polymer molecules and partial conversion of the intermediate material or sulfonyl groups on a polymer molecule to sulfonic acid groups. The sulfonyl fluoride polymer is substantially insoluble in all solvents except fluorocarbons.

The perfluorosulfonic acid catalyst are supported on solid supports primarily to maximize the surface area for reaction, maximize the number of sulfonic groups on or near the surface of the polymer for effective utilization of the catalyst facilitating minimum cost of catalyst and to modify engineering and mechanical properties to effect desired dimensional changes on solvation, fluids flow, heat removal, space time yield reaction, crush strength, etc. The preferred supported perfluorosulfonic acid catalyst comprises a film of a perfluorosulfonyl fluoride polymer precursor corresponding to a perfluorosulfonic acid polymer of 500 to 1,300 equivalent weight, preferably 900 to 1200 equivalent weight, deposited on a polymeric solid support, preferably a halocarbon or hydrocarbon polymer, by melt deposition, preferably by melt coextrusion, as a coating having a thickness of 0.1 mils to 2.0 mils, preferably 0.2 mils to 1.0 mils, and wherein said deposited perfluorosulfonyl fluoride polymer coating is converted to the corresponding perfluorosulfonic acid polymer to a depth of 0.01 mils to 1.0 mils, preferably to a depth of 0.05 to 0.5 mils.

The preferred supported catalyst of the instant process differ significantly from the supported catalyst of McClure et al. U.S. Pat. No. 4,038,213 in that the instant supported catalysts are attached to a substantially insoluble intermediate material or precursor material, a perfluorosulfonyl fluoride polymer, which firmly bonds the catalyst film to the support and substantially insolubilizes the normally soluble low equivalent weight, low molecular weight perfluorosulfonic acid molecules. The perfluorosulfonyl fluoride film may also serve as a substantially impermeable barrier to minimize permeation of reaction and regeneration fluids into the substrate. Prior to this invention, no practical way of making the preferred support perfluorosulfonic acid catalyst was known.

SUMMARY OF THE INVENTION

The desired supported perfluorocarbon sulfonic acid polymer catalyst is obtained by first forming into the desired catalyst shape or coating on a substrate, as an intermediate or precursor material, a polymer of perfluorocarbon containing sulfonyl fluoride groups or sulfonate salts of quaternary ammonium or phosphonium. Then the shaped polymer or coating is converted, to the degree desired, into the perfluorocarbon sulfonic acid catalyst. The forming is by heating if the intermediate material is thermoplastic, or by dissolving the ntermediate polymer material in a solvent and then forming a coating on a substrate by evaporative deposition.

DETAILED DESCRIPTION OF THE INVENTION

The supported fluorocarbon polymer catalyst comprise a fluorocarbon polymer containing carboxylic or sulfonic acid groups supported on a substrate. The fluorocarbon polymer comprises copolymers of alpha olefins (preferably of lower molecular weight such as tetrafluoroethylene, ethylene and propylene) and perfluorovinyl monomers containing acid and precursor acid groups. A preferred catalyst is the perfluorocarbon copolymer of tetrafluoroethylene and a perfluorovinyl ether having the repeating structure

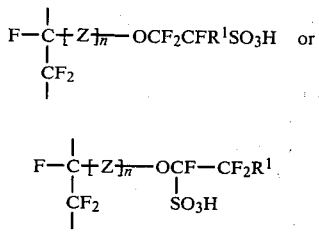

or mixtures thereof, wherein n is 0, 1 or 2, $R^1$ is —F or perfluoroalkyl of 1 to 10 carbon atoms, Z is —O—CF$_2$—CF$_2$—$_m$, —OCF$_2$CFY— or —OCFYCF$_2$— where m is an integer from 1 to 9, and Y is —F or trifluoromethyl. The copolymer can contain from 0.5 to 50 mole percent of the perfluorovinyl sulfonic acid. The polymer catalyst preferably has an equivalent weight (i.e., the weight of the polymer per sulfonic acid group in grams) ranging from 600 to 2500, most preferably 900 to 1500. The average molecular weight of these copolymers is not accurately known but are believed to be mostly in the range of 50,000 to 100,000 although solid polymers of good mechanical strength can have molecular weights above about 20,000 up to 500,000 to 1,000,000. The mechanical properties of tensile strength, toughness, flex life, etc. improve with increasing molecular weight.

Catalysts of the above-noted structure typically have a molecular weight of between 1,000 and 500,000 daltons, preferably above 10,000 daltons, and most preferably between 50,000 and 100,000 daltons.

Although, according to U.S. Pat. Nos. 4,038,213 and 4,052,475, finely ground powders of certain fluorinated polymers having sulfonic acid groups can be dispersed in ethanol, true solutions are not formed with the solid perfluorocarbon sulfonic acid polymers having the molecular and equivalent weights of the present invention.

For example, using polymers having molecular weights of about 50,000 to 100,000 daltons and equivalent weights ranging from about 700 to 1,350, the sulfonyl fluoride precursors and the corresponding perfluorosulfonic acid polymers having equivalent weights up to about 900 form solutions in FC-75 fluorocarbon fluid from 3M Company (sulfonyl fluoride polymers) and 95% ethanol (perfluorosulfonic acid polymers) of concentrations up to 100 grams per liter. A higher equivalent weight resin, (about 1050 EW) was refluxed with 95% ethanol and about 65% of the resin dissolved; the remainder was insoluble in ethanol indicating fractionation of the resin and dissolution of the low molecular-low equivalent weight fraction of the polymer. A perfluorosulfonic acid polymer of 1100 equivalent weight was refluxed with 95% ethanol and about 10% of the resin dissolved and the remainder was insoluble in refluxing ethanol. Less than 2% of a 1200 equivalent weight and a 1350 equivalent weight perfluorosulfonic resin was soluble in refluxing ethanol. The perfluorosulfonyl fluoride polymer precursors corresponding to the higher equivalent weight perfluorosulfonic acid resins formed solutions in FC-75 fluorocarbon fluid of concentrations ranging from about 40 to 100 grams per liter. Likewise the preferred perfluorocarbon sulfonic acid polymers resulting from the present invention are essentially infusible and cannot be melted to form true films bonded to supports. (See du Pont's magazine "Innovation" Volume 4/No. 3/Spring 1973 at pages 10-13, which describes properties and preparation of certain perfluorocarbon sulfonic acid polymers and derivatives, referred to under the du Pont tradename, NAFION resin.) By using the present process, supported sulfonic acid polymers are obtained which are firmly bonded to the supports, are contiguous films formed of inert polymer structures or backbones having pendant active sulfonic acid groups, are insoluble and are not leached from the support.

The preferred fabricable intermediate polymer material can be prepared in various ways, most usually from fluorocarbon vinyl ethers having the formula:

$$MSO_2CFR^1CF_2O[CFYCF_2O]_nCF=CF_2 \quad (III)$$

where $R^1$ and Y are the same as for formulas I and II, n is an integer of 1 to 3 inclusive, and M is a radical selected from the class consisting of fluorine, the amino radical and radicals having the formula —OMe where Me is a radical selected from the class consisting of quaternary ammonium and phosphonium radicals.

The perfluorocarbon vinyl ethers, and the intermediate polymer materials derived therefrom, are described in U.S. Pat. Nos. 3,041,317, 3,282,875, 3,264,053 and 3,882,093, the disclosures of which are hereby incorporated by reference.

The vinyl ethers used to prepare the intermediate polymer material can be polymerized, as described more fully in Connolly et al, U.S. Pat. No. 3,282,875, preferably in a perfluorocarbon solvent using a perfluorinated free radical initiator. Since the vinyl ethers are liquid at reaction conditions, it is further possible to polymerize and copolymerize the vinyl ethers in bulk without the use of a solvent. Polymerization temperatures vary from —50° to +200° C. depending on the initiator used. Pressure is not critical and is generally employed to control the ratio of the gaseous comonomer to the fluorocarbon vinyl ether. Suitable fluorocarbon solvents are known in the art and are generally perfluoroheptane or perfluorodimethylcyclobutane. Similarly, perfluorinated initiators are known in the art and include perfluoroperoxides and nitrogen fluorides. It is also possible to polymerize the vinyl ethers of the above structures in an aqueous medium using a peroxide or a redox initiator. The polymerization methods employed correspond to those established in the art for the polymerization of tetrafluoroethylene in aqueous media.

Preferred are the vinyl ethers copolymerized with tetrafluoroethylene and/or perfluoroalpha-olefins. A particularly preferred copolymer prepared by polymerizing perfluoroethylene with a perfluorovinyl ether containing sulfonyl fluoride groups would have the following illustrative repeating structure:

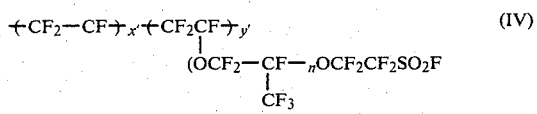

wherein n is 1 or 2, and the ratio of x' over y' varies from about 2 to 50. These sulfonyl fluorides are readily converted to alkali metal salts and the quaternary ammonium and phosphonium sulfonates. The potassium salt and the sulfonic acid derivatives of this structure are available commercially under the tradename of NAFION resin (E. I. duPont). Sulfonic acid catalysts derived from this structure offer the advantages of high concentrations of accessible acid groups in a solid phase.

After preparing the intermediate polymer material, it is formed into the desired catalyst shape. Preferably an intermediate polymer material which is thermoplastic is employed, since such materials lend themselves to shaping by heating and extruding or molding into the desired shapes and onto various substrates. Especially desirable are thin films formed or deposited onto the substrates. Also the intermediate polymer material can be dissolved, when sufficiently soluble, in suitable solvents and deposited from such solutions on a substrate; the solvent being removed before or after the material has been converted to the active sulfonic acid form.

One of the intermediates for the supported perfluorocarbon sulfonic acid catalyst is the corresponding sulfonyl fluoride. This sulfonyl fluoride, whose preparation is taught in the above patents, is thermoplastic. Thus, it can be extruded into a thin film, formed into a variety of shaped products, dip-coated or melted onto a support.

A preferred method for shaping the thermoplastic sulfonyl fluoride polymer on a support is by extrusion coating wherein the molten sulfonyl fluoride polymer is shaped as a contiguous thin film on the surface of the support. When the support is a thermoplastic material, the sulfonyl fluoride polymer and support may be melt shaped simultaneously by coextrusion, cut to size and shape, and, then the sulfonyl fluoride polymer converted, to the degree desired, to the perfluorosulfonic acid catalyst.

In using partial conversion of the perfluorosulfonyl fluoride precursor or intermediate ammonium salts for firmly bonding (anchoring) the sulfonic acid catalyst to a support, the unconverted sulfonyl fluoride polymer provides a high strength, solvent resistant and chemically stable anchor for the sulfonic acid catalyst to a solid support. The concept of first depositing the precursor or intermediate and then partially converting the precursor or intermediate to the sulfonic acid is unique in that conversion of the sulfonyl fluoride polymer proceeds essentially stepwise through the thickness of the polymer as the converting reactant permeates the polymeric structure whereby a transition zone is formed comprising polymer molecules containing both sulfonic acid and sulfonyl fluoride groups molecularly attached, such as by molecular entanglement and bonding, to the sulfonyl fluoride polymer and to the perfluorosulfonic acid polymer. The transitional zone polymers are especially beneficial for anchoring the lower equivalent weight perfluorosulfonic acid polymer molecules.

For economies in production and use of the supported catalyst, it is desirable to use a minimum of the high cost sulfonyl fluoride polymer precursor, especially for anchorage of the sulfonic acid polymer to a support. Deposition of the sulfonyl fluoride polymer onto a support having chemical groups (e.g., amino and hydroxy groups) reactive with the sulfonyl fluoride group wherein the reaction chemically bonds the perfluorocarbon polymer to the support can facilitate minimum use of the sulfonyl fluoride polymer. The sulfonyl fluoride polymer can also be melt extruded (deposited) onto the surface of a molten support whereby the sulfonyl fluoride polymer is melt welded to the support to facilitate molecular attachment and minimum usage of the high cost sulfonyl fluoride polymer.

Other intermediates for the fluorocarbon sulfonic acid catalyst are the corresponding quaternary ammonium or phosphonium sulfonates. The quaternary ammonium or phosphonium sulfonates can be prepared by treating the perfluorocarbon sulfonic acid or an alkali metal salt thereof with

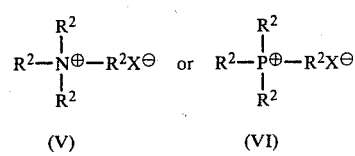

where each of the $R^2$ substituents is independently alkyl of 1 to 30 carbon atoms, alkaryl of 7 to 36 carbon atoms, aralkyl of 7 to 36 carbon atoms, phenyl or naphthyl, and X is an inorganic anion, preferably hydroxide or halide.

The preparation of the quaternary ammonium or phosphonium sulfonate is carried out by treating the perfluorocarbon sulfonic acid or the alkali metal salts thereof with a compound of Formula V or VI at 0° to 100° C. for 0.5 to 2 hours. The reaction proceeds at atmospheric pressure; however, higher or lower pressures may be used if desired.

The sulfonates formed by this process may be purified by washing with water to remove any residual by-products These sulfonates are thermoplastic, so that they may be shaped as taught above for the sulfonyl fluorides. They are also soluble in dipolar, aprotic solvents such as dimethylformamide and dimethyl-sulfoxide. Thus, a solution of such sulfonates can be used to coat a desired substrate using techniques well known in the art for coating using a solution of a polymer.

Particularly preferred quaternary ammonium and phosphonium sulfonates are formed using tetrabutylammonium hydroxide, benzyltrimethylammonium chloride, hexadecyltrimethylammonium chloride, and tetrabutylphosphonium iodide.

Although the perfluorocarbon polymers having pendant sulfonic acid groups are preferred, other acid groups such as carboxylic and phosphoric acid groups can be used.

The supported catalyst may contain metals, metal oxides, metal ions, metal chelates and other compounds which are normally homogeneous catalysts.

The substrate used to hold the thin film of catalyst can be any one of many materials appropriate for use as catalyst support, for example, any form of metal, such as screens or sheets, Teflon fibers, asbestos, glass (such as helices, beads or cloth), and the like. In addition, the perfluorocarbon sulfonyl fluoride can itself form the substrate and the desired thickness of sulfonyl fluoride may be converted to acid catalyst.

In one preferred embodiment, the supporting surface is a non-catalytic solid polymer such as sulfonyl fluoride polymer (which may be the intermediate used in forming the catalyst structure), polyethylene, polypropylene, polyamide, polyester, fluorocarbon polymers such as tetrafluoroethylene polymer, and the like.

In another preferred embodiment, the support is a metallic or inorganic solid substrate such as ceramic materials. Preferably the materials are those normally used in process equipment. Illustrative metallic supporting materials are monel, nickel, titanium, copper, brass, stainless steel compositions (e.g., Hasteloy), tantalum, zirconium and the like.

Especially suitable are thin films of the solid polymeric acid catalyst supported on an impermeable heat exchanger element which can consist of heat exchanger tubing, plates or the like of heat conductive metals. Such are particularly suited for carrying out the process of controlling exothermic reactions, e.g., hydroperoxide decompositions as described and claimed in my copending application U.S. Ser. No. 132,149, filed Mar. 20, 1980 (which is a continuation-in-part of U.S. Ser. No. 970,474, filed Dec. 18, 1978 and now abandoned), the description therein of the catalyst supported on a heat exchanger element being incorporated herein by reference. Such heat exchanger elements are essentially impermeable and provide support for the thin film of catalyst in a heat exchange relationship with a coolant or heat transfer fluid. The thin catalyst film is usually of mineral thickness from a molecular thickness up to 10 mils, most preferably less than 2 mils.

Once formed into the desired shape and properly bonded to the support, the intermediate is then converted to the active sulfonic acid form. The amount of intermediate converted is easily controlled by calculating the number of equivalents in the area to be converted (obtainable from the density and equivalent weight of the intermediate) and then reacting with an appropriate material to form the sulfonic acid groups. The rate of formation of the sulfonic acid groups is a function of time, temperature, and the concentration of the material being used to convert the intermediate to the sulfonic acid. Since each of these variables is readily controllable, conversion of the desired amount of intermediate can be done very accurately.

The materials necessary to convert the intermediate to the sulfonic acid form will be readily apparent to one skilled in the art and will be dependent upon the specific intermediate. For example, the sulfonyl fluoride is converted to the acid form by treating with an aqueous solution of an alkali metal hydroxide, preferably in the presence of an additional solvent such as dimethylsulfoxide or hexamethylphosphoramide, to form the potassium salt which is converted to the sulfonic acid form by treating with a strong acid having a pKa less than zero, such as hydrochloric acid or nitric acid.

The quaternary ammonium and phosphonium sulfonates are converted to sulfonic acid form by similar means. Thus, the sulfonic acids may be obtained by ion exchange. For example, the quaternary ammonium and phosphonium sulfonates can be treated with strong acid such as 20% nitric acid; sometimes it will be preferably first to convert the ammonium or phosphonium sulfonates to alkali metal salts such as by treatment with aqueous sodium chloride and then to displace the sodium bgy acid treatment.

As indicated above, the supported perfluorocarbon sulfonic acid catalyst in the desired shape can be obtained, in a preferred embodiment, by preparing a thermoplastic intermediate solid polymer of a perfluorocarbon vinyl ether containing sulfonyl fluoride groups, forming said intermediate polymer into the desired catalyst shape such as a thin film supported on a metal surface, and then converting at least part of the sulfonyl fluoride groups into the sulfonic acid form, thereby obtaining a non-plastic active catalyst which is firmly bonded to the support and is not leached from the support. Thus the perfluorocarbon sulfonic acid polymer catalyst can be formed as an insoluble thin film firmly bonded, preferably as a continuous layer, on the catalyst support. As such the catalyst is highly efficient.

EXAMPLES

The following examples are presented for the purpose of illustration only and are not in any way to be construed as limiting the scope of the invention described herein.

EXAMPLE 1

The sulfonyl fluoride form of the polymer described in Formula IV, formed into a tubing having an inner diameter of 0.024 inches, an outer diameter of 0.036 inches and a length of 18 feet, was immersed in water at 50° C. (The polymer was prepared with a tetrafluoroethylene-perfluorovinyl ether sulfonyl fluoride ratio of about 3 and had an equivalent weight of 1200. The molecular weight is not accurately known but is believed to be in the range of 50,000 to 100,000.) A mixture of 10% potassium hydroxide, 35% dimethyl-sulfoxide, and 55% water was pumped through the tubing for 45 minutes with the mixture being sufficient to provide an excess of base to expose the inner surface of the sulfonyl fluoride to saponifying conditions for this period of time. Then 2 molar hydrochloric acid in sufficient amount to displace the potassium ion was pumped through the tubing. A thickness of from 0.0011 to 0.0015 inches of the inner wall of the tubing was converted to the sulfonic acid form by this process.

EXAMPLE 2

Approximately 210 feet of the sulfonyl fluoride polymer described in Exaple 1 was wound around a solid aluminum spool 3.0 inches in diameter and 10 inches long. The aluminum spool was then cast in acrylic casting resin. Following the procedure of Example 1, a thickness of from 0.0011 to 0.0015 inch of the inner wall of the tubing was converted to the catalytic sulfonic acid form.

One of the supported catalysts of this invention is described in my copending application "Decomposition Process", Ser. No. 132,149, the disclosure of which is hereby incorporated by reference.

In a similar manner, quaternary ammonium and phosphonium salts of the perfluorocarbon sulfonic acid can be formed into tubing or other desired shapes by thermoplastic extrusion. Also solutions of the intermediates in suitable solvents such as dimethyl formamide can be evaporated onto a substrate, e.g., a metal support.

Other examples of carrying out the present invention are as follows:

EXAMPLE 3

A concentric tube arrangement can be made with an inner one-inch O.D. stainless steel tubing having formed on the outside thereof a 0.02 inch layer of the sulfonic acid form of perfluorocarbon polymer described in Formula IV and an outer metal tubing or casing of a diameter to leave therebetween an annular space of 0.05 inch radial distance. Reactants can be flowed through the annular space in sufficient volume to maintain the space full and in turbulent flow in contact with the active catalyst surface. At the same time, a coolant such as water or other heat transfer liquid is flowed through the inner tubing in a sufficient amount and volume to remove heat of reaction and maintain the temperature of the mixture of reactants and reaction products at a desired temperature such as, for example, 40° C.

Other examples of thin films of catalyst on heat exchanger elements in a suitable heat exchanger arrangement having an adequate flow of coolant on the opposite side of the element are indicated as follows:

A "Nafion" type catboxylate catalyst can be prepared as a film on the steel heat exchange element as follows: The copolymer of tetrafluoroethylene and perfluorovinyl ether methyl ester (in a mol ratio such as to give about 10–30% ester in the copolymer) is applied such as by molding as a thin film on the heat exchanger element. Then the surface is treated with NaOH to saponify the ester groups and then, after washing, is treated with dilute acid to form carboxylic acid groups. (More details on the formation of the carboxylate are given by Hiroshi Ukihashi in Chemtech, Febrary 1980 pp. 118-120.)

Other variations of the thin films of active solid perfluorocarbon polymers containing pendant acid groups which films are supported on the surface of suitable substrates can be readily devised in view of this specification by one skilled in the art.

Thus, a supported fluorosulfonic acid catalyst can be prepared by coextrusion of a fluorosulfonyl fluoride precursor resin and a polyethylene resin. The coextrusion can be carried out by conventional techniques wherein the fluorosulfonyl fluoride resin is melt extruded simultaneously with the melt extrusion of the polyethylene resin through a die designated so that the polyethylene resin is shaped as a fiber or filament and onto which a thin film of the molten fluoroculfonyl fluoride resin is deposited. The composite extrudate is quenched, granulated to the desired size and the fluorosulfonyl fluoride film converted to the desired depth to the fluorosulfonic acid catalyst. A typical supported catalyst would be formed by co-extrusion of the polyethylene resin and the fluorosulfonyl fluoride resin at a temperature of about 250° to 350° C. into a composite extrudate consisting of a polyethylene fiber about 5 mils in diameter coated with a sulfonyl fluoride resin film of about 0.5 mils thick. The extrudate would be cut to a length of about 0.25 inches and the fluorosulfonyl fluoride film converted to the fluorosulfonic acid catalyst to a depth of about 0.35 mils.

As another illustration, a supported fluorosulfonic acid catalyst can be prepared by melt deposition of a coating of a sulfonyl fluoride resin onto a nominal 0.5 inch monel metal tubing for heat exchangers. The melt deposition can be carried out using conventional melt extrusion equipment wherein the metal tube is passed through a die and the molten fluorosulfonyl fluoride polymer pressed onto the tube. The coated metal tubing can be fabricated into a tube sheet using conventional techniques for the uncoated tubing and the array of tubes assembled into a shell and tube exchanger. The sulfonyl fluoride coating can be converted to the desired depth. Typically, the fluorosulfonyl fluoride resin is extruded at a temperature of about 250° to 350° C. to form a contiguous coating on the outer surface of the metal tube. The thickness of the fluorosulfonyl fluoride resin film can be about 0.5 mils thick and the film converted to the sulfonic acid catalyst to a depth of about 0.25 mils.

What is claimed is:

1. A process of preparing a supported, infusible, substantially insoluble, catalyst of a perfluorocarbon polymer containing pendant acid groups, which comprises:
   first, coating a solid substrate with a thin film of an intermediate perfluorocarbon polymer containing pendant groups which are convertible to acid groups having an equivalent weight of at least 900,
   and second, converting only the surface layer of said pendant groups of said intermediate in said coating into acid groups, thereby obtaining a composite of said infusible, substantially insoluble acid polymer catalyst bound to said supporting substrate by unconverted polymer.

2. A process of preparing a supported, infusible, substantially insoluble, catalyst of a perfluorocarbon polymer containing pendant sulfonic acid groups, which comprises:
   first, coating a solid substrate with a thin film of an intermediate perfluorocarbon polymer containing pendant sulfonyl fluoride groups or sulfonate salts of quaternary ammonium or phosphonium, corresponding to perfluorocarbon polymers containing pendant sulfonic acid groups having an equivalent weight of at least 900,
   and second, converting part of said pendant sulfonyl fluoride or sulfonate groups in said coating into sulfonic acid groups, thereby obtaining a substantially insoluble composite of said sulfonic acid polymer catalyst bound to said supporting substrate by unconverted intermediate polymer.

3. The process of claim 2 wherein said coating is formed by melt deposition of a fusible perfluorocarbon polymer containing pendant sulfonyl fluoride groups.

4. The process of claim 3 wherein said perfluorosulfonyl fluoride polymer is extruded onto said substrate to form a coating of 0.1 to 2.0 mils in thickness.

5. The process of claim 2 wherein said intermediate perfluorocarbon polymer contains pendant sulfonyl fluoride or sulfonate groups corresponding to a equivalent weight of 1100 to 1500 in the sulfonic acid form.

6. The process of claim 2 wherein said intermediate polymer is shaped by extrusion or coating as a thin film onto a metal surface.

7. The process of claim 2 wherein said intermediate polymer has an average molecular weight of 1,000 to 500,000 daltons.

8. The catalyst prepared by the method of claim 2.

9. A solid polymeric acid catalyst composite consisting essentially of a solid substrate and thereon a thin film coating of 0.1 to 10 mils thick, of fusible solid perfluorocarbon polymer containing pendant groups which are convertable to acid groups, the surface layer of said polymer coating having been converted to an infusible solid perfluorocarbon polymer containing pendant acid groups and equivalent weight of at least 900, the unconverted portion of said coating binding said acid polymer layer to said substrate.

10. A supported solid polymeric acid catalyst composite consisting essentially of (1) a solid impermeable substrate, (2) a thin film coating, of 0.1 to 10 mils thick, of a substantially insoluble infusible solid perfluorocarbon polymer containing pendant sulfonic acid groups and having an equivalent weight of at least 900 and (3) a fusible solid perfluorocarbon polymer containing pendant sulfonyl fluoride groups between said acid polymer thin film and said substrate and binding said acid polymer thin film to said substrate.

11. The solid polymer acid catalyst composite of claim 9 adapted for carrying out highly exothermic reactions under controlled conditions, wherein said thin film is 0.1 to 2 mils thick and adapted for contact with the reactants and wherein said substrate is a heat exchanger element adapted for contact on the opposite side from thin film coating with a coolant for removing heat of reaction.

12. The catalyst of claim 9, wherein said thin film has a molecular weight of 50,000 to 100,000 daltons.

13. The solid polymeric acid catalyst of claim 9 wherein the supporting substrate is a non-catalytic solid polymer.

14. The catalyst of claim 9 wherein the supporting substrate is a metallic or inorganic solid substrate.

15. The catalyst of claim 14, wherein said support is heat conductive metal.

* * * * *